United States Patent
Deng et al.

(10) Patent No.: US 10,336,696 B2
(45) Date of Patent: Jul. 2, 2019

(54) BICARBAZOLE COMPOUND, PHOTO-CURABLE COMPOSITION, CURED PRODUCT THEREOF, CURABLE COMPOSITION FOR PLASTIC LENS, AND PLASTIC LENS

(71) Applicant: DIC Corporation, Tokyo (JP)

(72) Inventors: Changjun Deng, Qingdao (CN); Masanori Miyamoto, Sakura (JP); Nobuo Kobayashi, Ichihara (JP); Xia Yang, Qingdao (CN)

(73) Assignee: DIC Corporation, Tokyo (JP)

( * ) Notice: Subject to any disclaimer, the term of this patent is extended or adjusted under 35 U.S.C. 154(b) by 141 days.

(21) Appl. No.: 15/305,715

(22) PCT Filed: Apr. 30, 2014

(86) PCT No.: PCT/CN2014/076634
§ 371 (c)(1),
(2) Date: Oct. 21, 2016

(87) PCT Pub. No.: WO2015/165089
PCT Pub. Date: Nov. 5, 2015

(65) Prior Publication Data
US 2017/0073310 A1   Mar. 16, 2017

(51) Int. Cl.
| | |
|---|---|
| C07D 209/86 | (2006.01) |
| C08F 290/00 | (2006.01) |
| G02B 1/04 | (2006.01) |
| G02B 3/08 | (2006.01) |
| C08F 222/22 | (2006.01) |
| C08F 222/38 | (2006.01) |

(52) U.S. Cl.
CPC .......... *C07D 209/86* (2013.01); *C08F 222/22* (2013.01); *C08F 222/385* (2013.01); *C08F 290/00* (2013.01); *G02B 1/041* (2013.01); *G02B 3/08* (2013.01)

(58) Field of Classification Search
CPC .... C07D 209/86; C08F 290/00; C08F 222/22; C08F 222/385; G02B 1/041; G02B 3/08
See application file for complete search history.

(56) References Cited

FOREIGN PATENT DOCUMENTS

| | | |
|---|---|---|
| JP | 04-325508 A | 11/1992 |
| JP | 05-341105 A | 12/1993 |
| JP | 2007-084815 A | 4/2007 |
| KR | 2013-0134451 A | 12/2013 |

OTHER PUBLICATIONS

Bicarbazoles: Systematic Structure—Property Investigations on a Series of Conjugated Carbazole Dimers Shin-ichiro Kato, Hiroto Noguchi, Atsushi Kobayashi, Toshitada Yoshihara, Seiji Tobita, and Yosuke Nakamura The Journal of Organic Chemistry 2012 77 (20), 9120-9133 (Year: 2012).*

International Search Report dated Feb. 4, 2015, issued for PCT/CN2014/076634.

* cited by examiner

*Primary Examiner* — Sanza L. McClendon
(74) *Attorney, Agent, or Firm* — Locke Lord LLP

(57) ABSTRACT

A photopolymerizable material contains, as a main polymerization component, a bicarbazole compound represented by structural formula (1).

[Chem. 2]

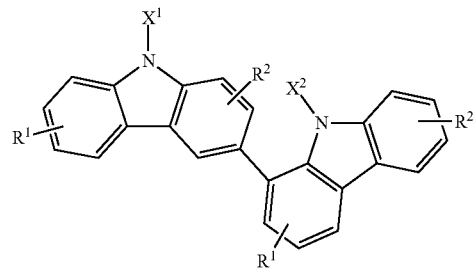

(1)

In structural formula (1), $X^1$ and $X^2$ are each independently a photopolymerizable functional group, a structural site having a photopolymerizable functional group, or a hydrogen atom, at least one of $X^1$ and $X^2$ is a photopolymerizable functional group or a structural site having a photopolymerizable functional group, $R^1$ and $R^2$ are each independently a hydrogen atom, an alkyl group having 1 to 4 carbon atoms, an alkoxy group having 1 to 4 carbon atoms, a bromine atom, or a chlorine atom, and at least one of $R^1$ and $R^2$ is a hydrogen atom.

18 Claims, 4 Drawing Sheets

BICARBAZOLE COMPOUND, PHOTO-CURABLE COMPOSITION, CURED PRODUCT THEREOF, CURABLE COMPOSITION FOR PLASTIC LENS, AND PLASTIC LENS

TECHNICAL FIELD

The present invention relates to a bicarbazole compound whose cured product has a high refractive index and which is useful for a plastic lens, a photo-curable composition containing the bicarbazole compound, a cured product obtained by curing the photo-curable composition, a composition for a plastic lens, the composition including the photo-curable composition, and a plastic lens having a high refractive index.

BACKGROUND ART

Recently, resin materials have been widely used in optical components such as an over-coating agent for optical use, a hard-coating agent, an antireflection film, a spectacle lens, an optical fiber, an optical waveguide, and a hologram because of their good processability and productivity. Furthermore, from the viewpoints of the tendency of a reduction in the size and a reduction in the thickness of optical components and the adjustment of antireflection properties, resin materials having high refractive indices have been desired. In particular, recently, in liquid crystal display elements used in displays of liquid crystal televisions, notebook personal computers, portable video game machines, cellular phones, etc., requirements for a reduction in the size, a high resistance property, and realization of a high brightness have been increasing. To achieve this, it is essential to realize high refractive indices for materials of prism sheets.

From the viewpoint of realization of high refractive indices for materials of prism sheets, in the related art, for example, it is known that a bifunctional acrylate compound having a 9,9-bisphenoxyfluorene skeleton is used as a photopolymerizable monomer (refer to PTL 1 and PTL 2). However, such an acrylate monomer having a 9,9-bisphenoxyfluorene skeleton is a liquid having a high viscosity of several tens of pascal seconds or more at room temperature. Accordingly, when the acrylate monomer is used as a shape-forming material of a prism sheet or the like, it is necessary to dilute the monomer with a large amount of a reactive diluent or the like so that the resulting monomer solution comes to have an appropriate viscosity. Consequently, the refractive index of the resulting cured product decreases.

Compositions that contain N-vinylcarbazole (9-vinylcarbazole) or a derivative thereof are known examples of materials of prism sheets having high refractive indices (refer to PTL 3). However, N-vinylcarbazole has high crystallinity and is difficult to handle. In addition, at present, the refractive indices of cured products obtained by curing any of these compositions are not at a satisfactory level.

As described above, existing high-refractive index polymerizable compounds tend to have high viscosities by themselves or are easily crystallized. As a result, in the case where such compounds are used in practical compositions, it is difficult to sufficiently increase the refractive indices of the resulting cured products.

CITATION LIST

Patent Literature

[PTL 1]
Japanese Unexamined Patent Application Publication No. 04-325508
[PTL 2]
Japanese Unexamined Patent Application Publication No. 2007-84815
[PTL 3]
Japanese Unexamined Patent Application Publication No. 05-341105

SUMMARY OF INVENTION

Technical Problem

Accordingly, it is an object of the present invention to provide a photopolymerizable material which contains a compound that is non-crystalline and whose cured product exhibits a markedly high refractive index, a cured product of the photopolymerizable material, and a material of a prism sheet having a high refractive index which has not hitherto been achieved.

Solution to Problem

To achieve the above object, the inventors of the present invention conducted intensive studies. As a result, it was found that a photopolymerizable compound having a 1,3'-bicarbazole skeleton as a main chemical structure had low crystallinity, and consequently, in the adjustment of the viscosity, it was sufficient to use only a small amount of reactive diluent or the like. Accordingly, it was found that the photopolymerizable compound could be used as an optical material whose cured product had a significantly high refractive index. These findings resulted in the completion of the present invention.

Specifically, the present invention relates to a bicarbazole compound represented by structural formula (1) below:

[Chem. 1]

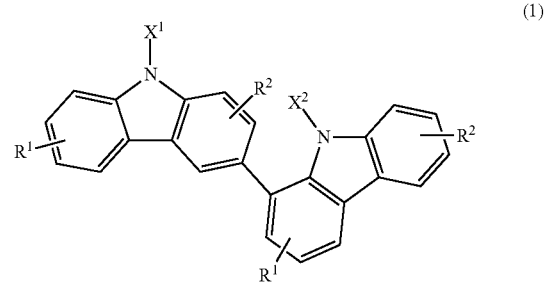

(1)

In structural formula (1), $X^1$ and $X^2$ are each independently a photopolymerizable functional group, a structural site having a photopolymerizable functional group, or a hydrogen atom, at least one of $X^1$ and $X^2$ is a photopolymerizable functional group or a structural site having a photopolymerizable functional group, $R^1$ and $R^2$ are each independently a hydrogen atom, an alkyl group having 1 to 4 carbon atoms, an alkoxy group having 1 to 4 carbon atoms, a bromine atom, or a chlorine atom, and at least one of $R^1$ and $R^2$ is a hydrogen atom.

The present invention further relates to a photo-curable composition containing the bicarbazole compound (A) and a photopolymerization initiator (B).

The present invention further relates to a cured product obtained by curing the photo-curable composition.

The present invention further relates to a curable composition for a plastic lens, the curable composition including the photo-curable composition.

The present invention further relates to a plastic lens obtained by curing the curable composition for a plastic lens.

Advantageous Effects of Invention

According to the present invention, it is possible to provide a photopolymerizable material which contains a compound that is non-crystalline and whose cured product exhibits a markedly high refractive index, a cured product of the photopolymerizable material, and a material of a prism sheet having a high refractive index which has not hitherto been achieved.

DESCRIPTION OF EMBODIMENTS

Figure 1:
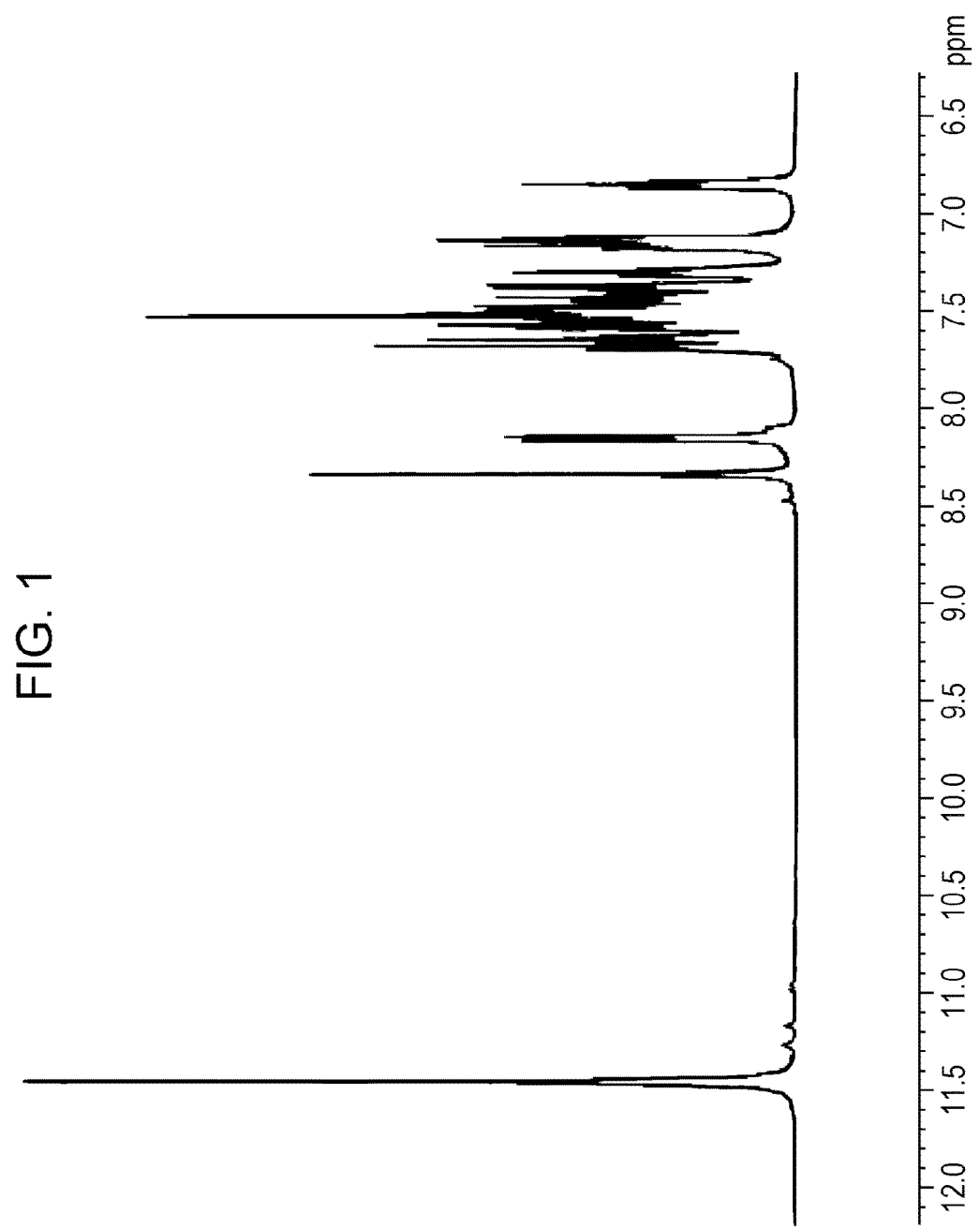
FIG. 1 is a $^1$H-NMR chart of a 1,3'-bicarbazole composition 1 prepared in Synthesis Example 1.

As described above, a bicarbazole compound of the present invention is represented by structural formula (1) below:

[Chem. 2]

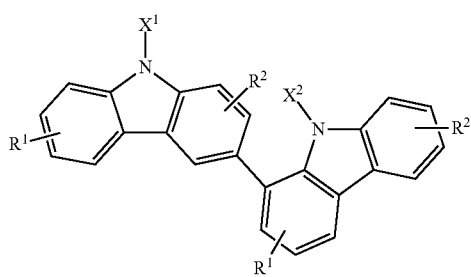

(1)

In structural formula (1), $X^1$ and $X^2$ are each independently a photopolymerizable functional group, a structural site having a photopolymerizable functional group, or a hydrogen atom, at least one of $X^1$ and $X^2$ is a photopolymerizable functional group or a structural site having a photopolymerizable functional group, $R^1$ and $R^2$ are each independently a hydrogen atom, an alkyl group having 1 to 4 carbon atoms, an alkoxy group having 1 to 4 carbon atoms, a bromine atom, or a chlorine atom, and at least one of $R^1$ and $R^2$ is a hydrogen atom. In the present invention, the compound has a bicarbazole structure in which a 1-position carbon atom and a 3-position carbon atom of carbazole structures are bonded to each other, and thus crystallization does not easily occur. Furthermore, solubility of the compound in solvents is also good, and the compound has a markedly high refractive index after being cured.

Specific examples of the photopolymerizable functional groups constituting $X^1$ and $X^2$ in structural formula (1) above include radical-polymerizable functional groups such as a vinyl group and an acryloyl group; and photo-cationic-polymerizable functional groups such as a glycidyl group and a 2-methylglycidyl group.

Examples of the structural sites having a photopolymerizable functional group, the structural sites constituting $X^1$ and $X^2$ in structural formula (1) above, include structural sites having a photo-cationic-polymerizable functional group such as a 3-methyloxetanyl-methyl group or a 3-ethyloxetanyl-methyl group; and structural sites having a radical-polymerizable functional group, such as a (meth)acryloyl group-containing structural site represented by structural formula (2) below:

[Chem. 3]

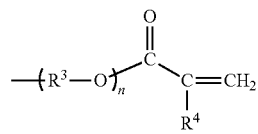

(2)

In structural formula (2), $R^3$ represents a linear or branched alkylene group having 2 to 6 carbon atoms, $R^4$ represents a hydrogen atom or a methyl group, and n represents an integer of 0 to 10.

Specific examples of the (meth)acryloyl group-containing structural site include a (meth)acryloyloxyethyl group, a (meth)acryloyl polyoxyethylene group, a (meth)acryloyloxypropylene group, and a (meth)acryloyl polyoxypropylene group. Among these, a (meth)acryloyloxyethyl group is preferable from the viewpoint that reactivity is good and the resulting cured product has a high refractive index.

Comparing the radical-polymerizable functional groups with the photo-cationic-polymerizable functional groups, the radical-polymerizable functional groups are preferable from the viewpoint of good curability. One of $X^1$ and $X^2$ in structural formula (1) may be a hydrogen atom as described above. However, in the present invention, from the viewpoint of good curability, $X^1$ and $X^2$ are each preferably a photopolymerizable functional group or a structural site having a photopolymerizable functional group.

Specific examples of the bicarbazole compound will be described. Examples of the bicarbazole compound in which $X^1$ and $X^2$ in structural formula (1) are each a vinyl group include compounds represented by structural formulae (I-1) to (I-5) below:

[Chem. 4]

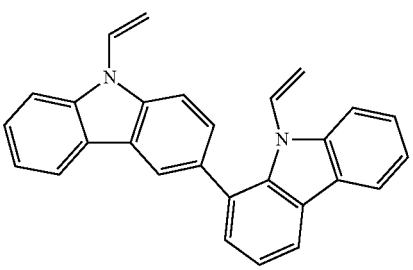

I-1

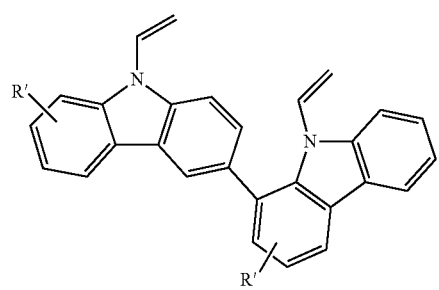

I-2

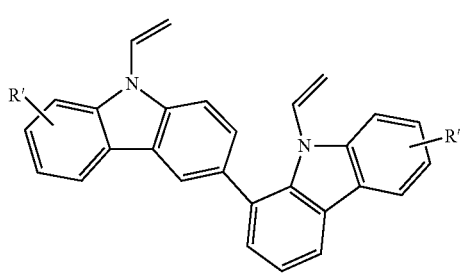

I-3

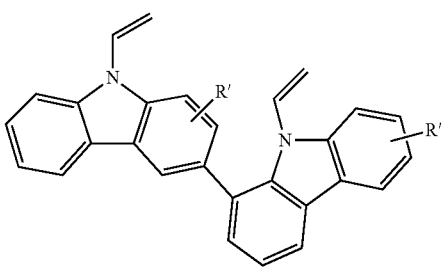

I-4

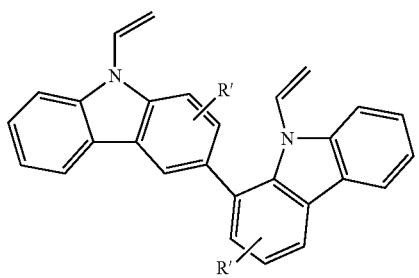

I-5

In structural formulae (I-1) to (I-5), R' may be a substituent selected from the group consisting of a methyl group, an ethyl group, a propyl group, a tert-butyl group, a methoxy group, a chlorine atom, and a bromine atom.

Examples of the bicarbazole compound that has acryloyl groups as $X^1$ and $X^2$ in structural formula (1) include compounds represented by structural formulae (II-1) to (II-5) below:

[Chem. 5]

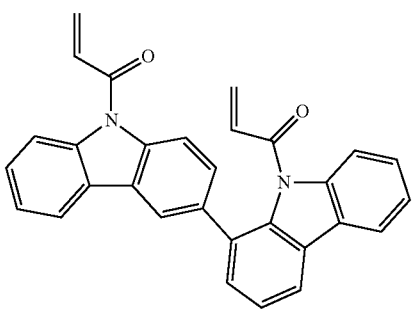

II-1

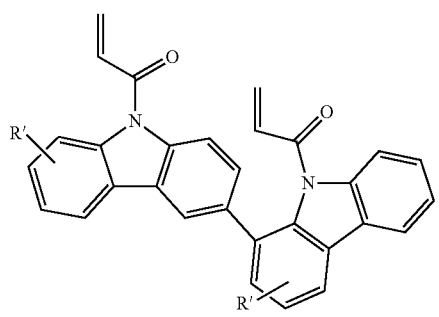

II-2

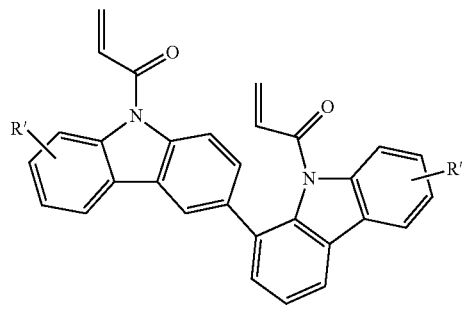

II-3

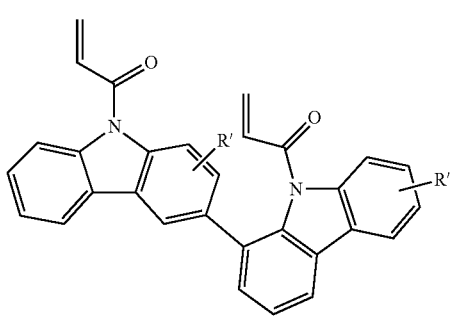

II-4

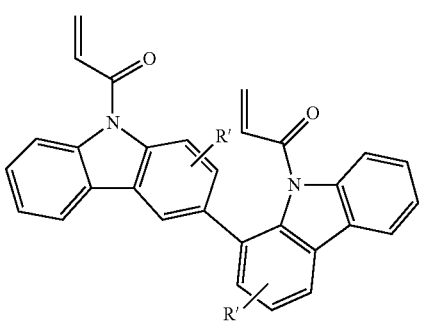

II-5

In structural formulae (II-1) to (II-5), R' may be a substituent selected from the group consisting of a methyl group, an ethyl group, a propyl group, a tert-butyl group, a methoxy group, a chlorine atom, and a bromine atom.

Examples of the bicarbazole compound that has methacryloyl groups as $X^1$ and $X^2$ in structural formula (1) include compounds represented by structural formulae (III-1) to (III-5) below:

[Chem. 6]

III-1
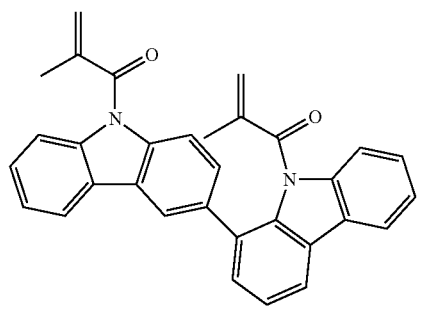

III-2
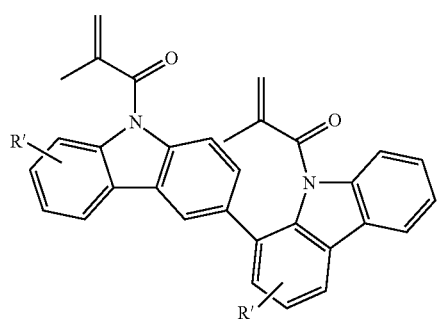

III-3
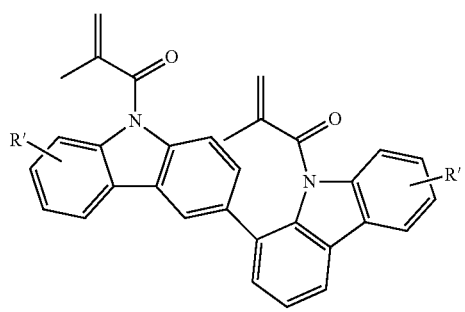

III-4
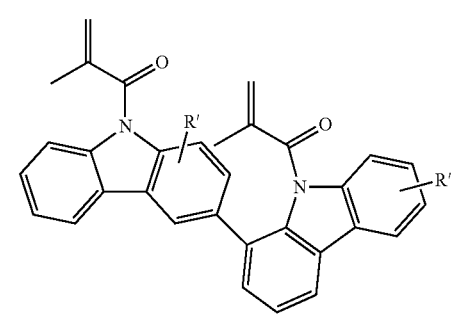

III-5
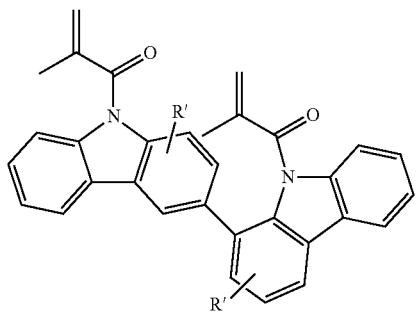

In structural formulae (III-1) to (III-5), R' may be a substituent selected from the group consisting of a methyl group, an ethyl group, a propyl group, a tert-butyl group, a methoxy group, a chlorine atom, and a bromine atom.

Examples of the bicarbazole compound that has acryloyloxyethyl groups as $X^1$ and $X^2$ in structural formula (1) include compounds represented by structural formulae (IV-1) to (IV-5) below:

[Chem. 7]

IV-1
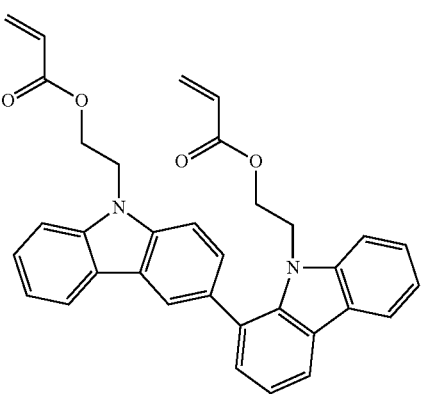

IV-2
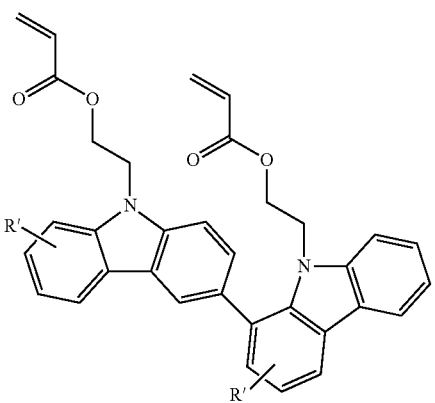

IV-3
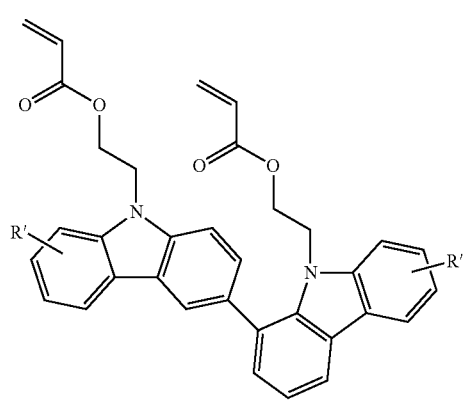

IV-4
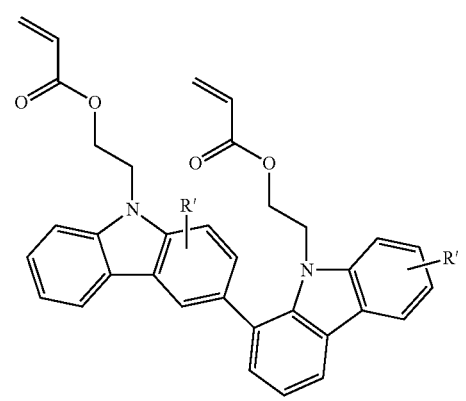

IV-5
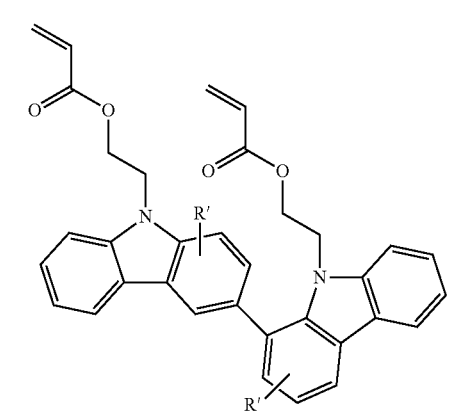

In structural formulae (IV-1) to (IV-5), R' may be a substituent selected from the group consisting of a methyl group, an ethyl group, a propyl group, a tert-butyl group, a methoxy group, a chlorine atom, and a bromine atom.

Examples of the bicarbazole compound that has methacryloyloxyethyl groups as $X^1$ and $X^2$ in structural formula (1) include compounds represented by structural formulae (V-1) to (V-5) below:

[Chem. 8]

V-1
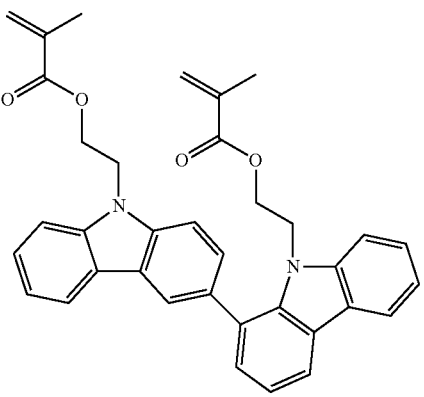

V-2
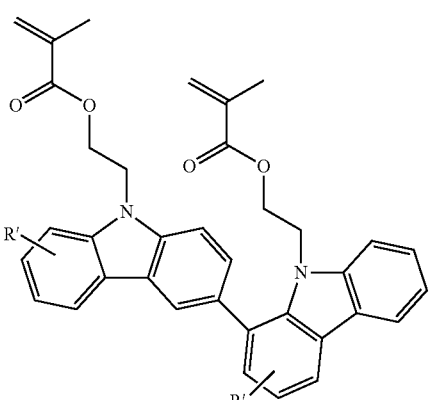

V-3
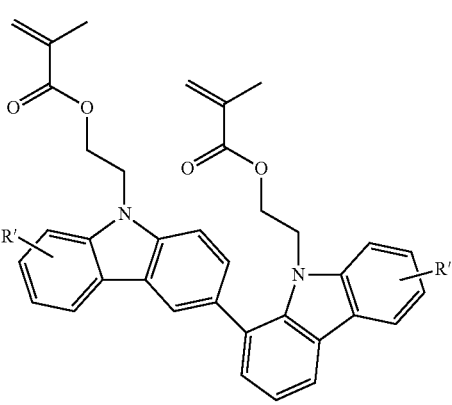

V-4
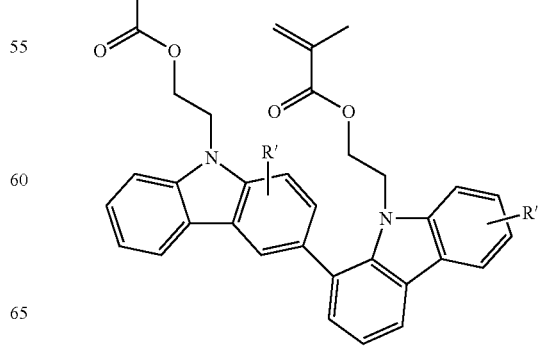

V-5

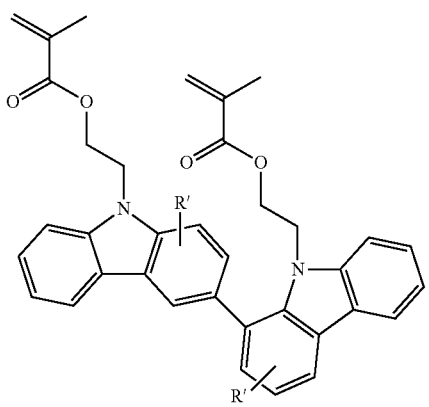

In structural formulae (V-1) to (V-5), R' may be a substituent selected from the group consisting of a methyl group, an ethyl group, a propyl group, a tert-butyl group, a methoxy group, a chlorine atom, and a bromine atom.

Examples of the bicarbazole compound that has glycidyl groups as $X^1$ and $X^2$ in structural formula (1) include compounds represented by structural formulae (VI-1) to (VI-5) below:

[Chem. 9]

VI-1

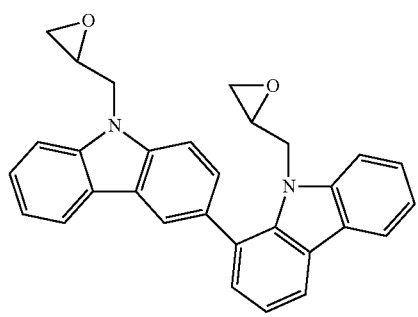

VI-2

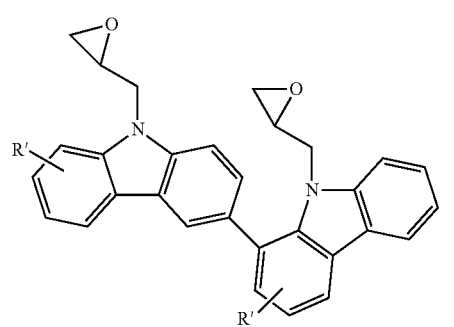

VI-3

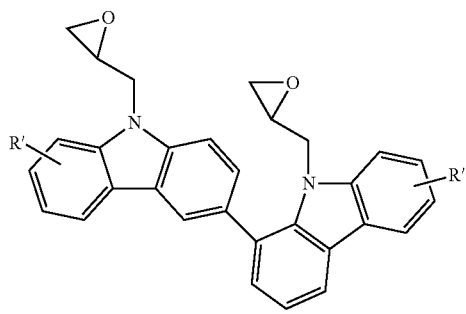

VI-4

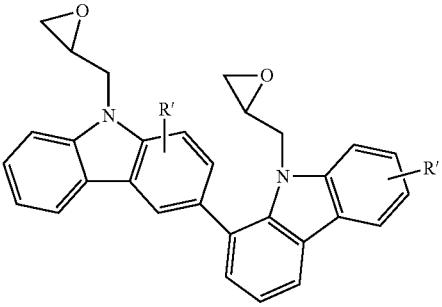

VI-5

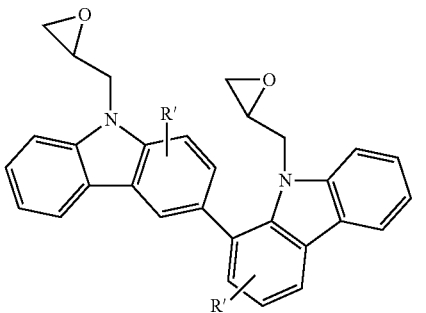

In structural formulae (VI-1) to (VI-5), R' may be a substituent selected from the group consisting of a methyl group, an ethyl group, a propyl group, a tert-butyl group, a methoxy group, a chlorine atom, and a bromine atom.

Examples of the bicarbazole compound that has 2-methylglycidyl groups as $X^1$ and $X^2$ in structural formula (1) include compounds represented by structural formulae (VII-1) to (VII-5) below:

[Chem. 10]

VII-1

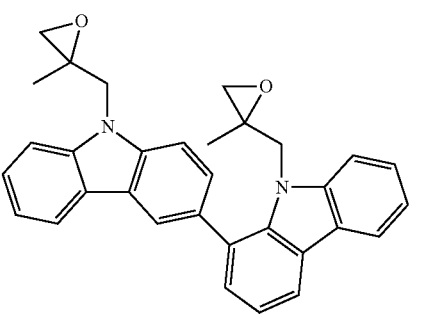

VII-2

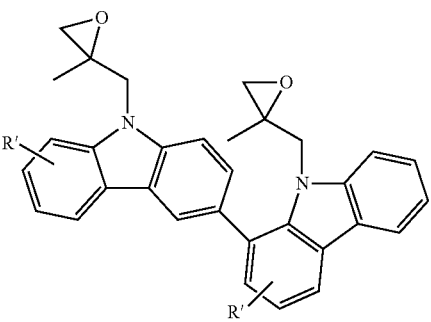

-continued

VII-3
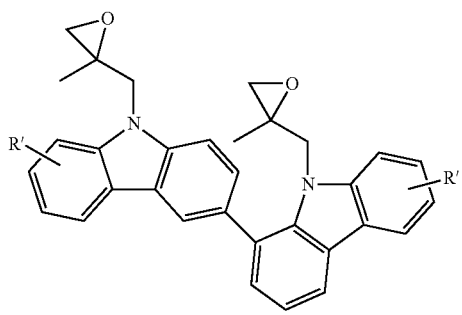

VII-4
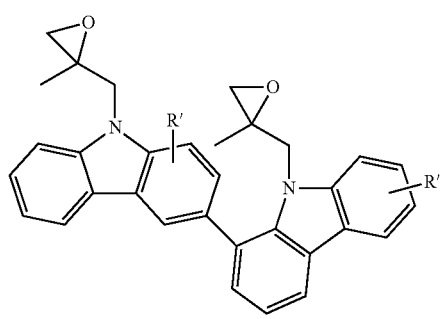

VII-5
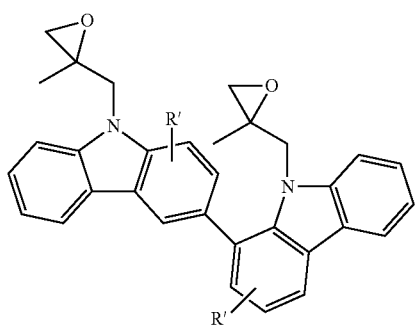

In structural formulae (VII-1) to (VII-5), R' may be a substituent selected from the group consisting of a methyl group, an ethyl group, a propyl group, a tert-butyl group, a methoxy group, a chlorine atom, and a bromine atom.

Examples of the bicarbazole compound that has 3-ethyl-oxetanyl-methyl groups as $X^1$ and $X^2$ in structural formula (1) include compounds represented by structural formulae (VIII-1) to (VIII-5) below:

[Chem. 11]

VIII-1
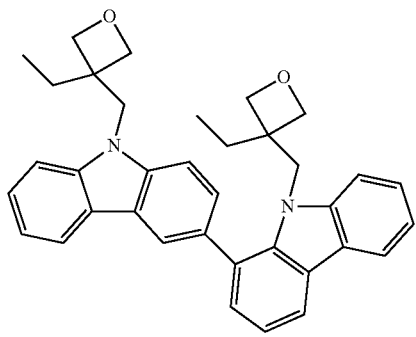

-continued

VIII-2
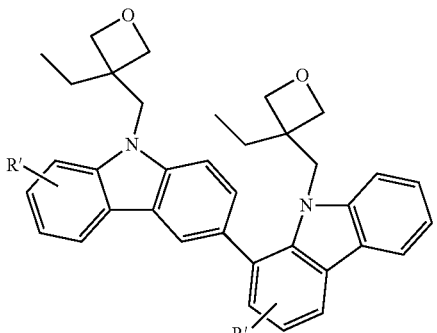

VIII-3
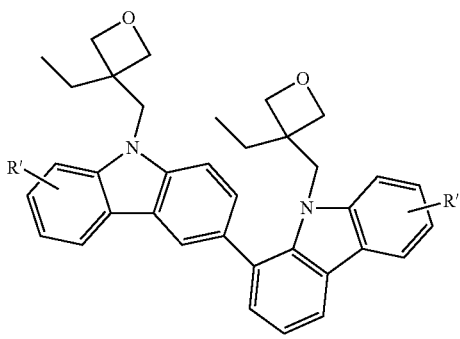

VIII-4
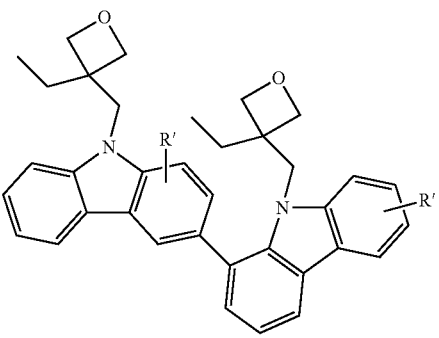

VIII-5
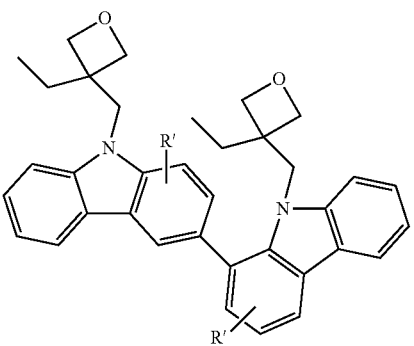

In structural formulae (VIII-1) to (VIII-5), R' may be a substituent selected from the group consisting of a methyl group, an ethyl group, a propyl group, a tert-butyl group, a methoxy group, a chlorine atom, and a bromine atom.

In the present invention, among these compounds, compounds which are represented by structural formulae (I-1) to (I-5) and in which $X^1$ and $X^2$ in structural formula (1) are each a vinyl group; compounds which are represented by structural formulae (II-1) to (II-5) and in which $X^1$ and $X^2$ in structural formula (1) are each an acryloyl group; compounds which are represented by structural formulae (III-1)

to (III-5) and in which $X^1$ and $X^2$ in structural formula (1) are each a methacryloyl group; and compounds which are represented by structural formulae (IV-1) to (IV-5) and in which $X^1$ and $X^2$ in structural formula (1) are each an acryloyloxyethyl group are preferable from the viewpoint of good curability.

In addition, bicarbazole compounds having no substituents on aromatic nuclei thereof are preferable from the viewpoint of a high refractive index. Accordingly, compounds represented by structural formulae (I-1), (II-1), (III-1), and (IV-1) are particularly preferable.

The bicarbazole compound (A) described in detail above may contain, as a main polymerization component having a bicarbazole skeleton, a carbazole compound represented by structural formula (3) below in a ratio of 30% by mass or less relative to the total mass of the bicarbazole compound and the carbazole compound.

[Chem. 12]

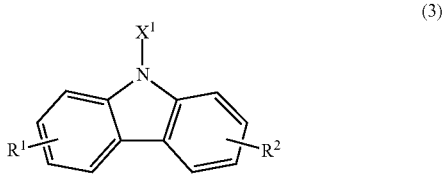

(3)

In structural formula (3), $X^1$ is a photopolymerizable functional group, a structural site having a photopolymerizable functional group, or a hydrogen atom, $R^1$ and $R^2$ are each independently a hydrogen atom, an alkyl group having 1 to 4 carbon atoms, an alkoxy group having 1 to 4 carbon atoms, a bromine atom, or a chlorine atom, and at least one of $R^1$ and $R^2$ is a hydrogen atom.

The photopolymerizable functional group and the structural site having a photopolymerizable functional group that constitute $X^1$ in structural formula (3) are the same as those in structural formula (1).

The bicarbazole compound described in detail above can be produced by a method described below. Specifically, a 1,2,3,4-tetrahydrocarbazole represented by structural formula (4) below is subjected to an oxidation reaction in the presence of activated carbon.

[Chem. 13]

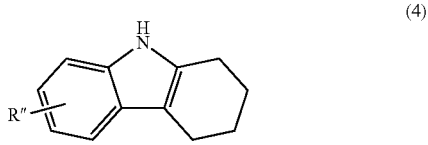

(4)

In structural formula (4), R" is the same as $R^1$ or $R^2$ in structural formula (1) above. Thus, a bicarbazole (hereinafter abbreviated as "bicarbazole (a1)") represented by structural formula (5) below is produced (Step 1).

[Chem. 14]

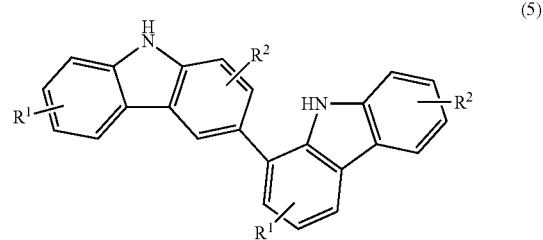

(5)

In structural formula (5), $R^1$ and $R^2$ are the same as those in structural formula (1) above. In this step, in the case where a carbazole (hereinafter abbreviated as "carbazole (a2)") represented by structural formula (6) below is also produced, it is referable to remove the carbazole (a2) by purification until the content of the carbazole (a2) in the product becomes 15% by mass or less.

[Chem. 15]

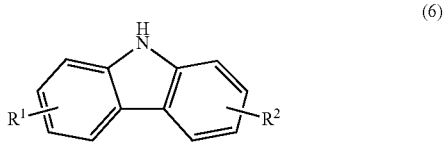

(6)

In structural formula (6), $R^1$ and $R^2$ are the same as those in structural formula (1) above.

Activated carbon used in Step 1 may be used alone. Alternatively, activated carbon may be used in the form of a so-called Pd—C catalyst in which a catalyst such as a palladium catalyst is supported on the activated carbon.

In Step 1, an organic solvent is preferably used. Examples of the organic solvent that can be used in this step include benzene, xylene, 1,3,5-trimethylbenzene, and 1,2-dichlorobenzene.

The reaction temperature in Step 1 is not particularly limited. However, since the reaction rapidly proceeds under a high-temperature condition, the reaction temperature in Step 1 is usually preferably in the range of 140 to 180 degrees Celsius.

Subsequently, the bicarbazole (a1) represented by structural formula (5) or a mixture of the bicarbazole (a1) represented by structural formula (5) and the carbazole (a2) represented by structural formula (6) is allowed to react with a compound serving as a source of a photopolymerizable functional group (Step 2). Thus, a desired bicarbazole compound (A) can be obtained.

A reaction method in Step 2 varies depending on the functional group to be introduced. For example, in the case where a vinyl group is introduced, the following method may be employed. Specifically, ethylene carbonate is allowed to react with a reaction product obtained in Step 1, a produced terminal hydroxyl group is allowed to react with para-toluene sulfonyl chloride to conduct tosylation, then a detosylation reaction is conducted in the presence of a basic catalyst to produce a vinyl group.

In the case where an acryloyl group is introduced, the following method may be employed. Specifically, 3-chloropropionyl chloride is allowed to react with a reaction product obtained in Step 1 to introduce a 3-chloropropionyl group, and then a double bond is formed in the presence of a basic catalyst.

In the case where the structural site represented by structural formula (2) is introduced as a structural site having a photopolymerizable functional group, the structural site constituting $X^1$ and/or $X^2$ in structural formula (1), the following method may be employed. Specifically, an alkylene carbonate is allowed to react with a reaction product obtained in Step 1, and, as required, an alkylene oxide is further allowed to react by a common method to produce a hydroxyl group at an end. Subsequently, (meth)acrylic acid is allowed to react in the presence of a basic catalyst.

In the case where the structural site having an oxetanyl group such as a 3-methyloxetanyl-methyl group or a 3-ethyloxetanyl-methyl group is introduced as a structural site having a photopolymerizable functional group, the structural site constituting $X^1$ and/or $X^2$ in structural formula (1), a method including allowing a 3-chloromethyl-3-alkyloxetane to react with a reaction product obtained in Step 1 in the presence of a basic catalyst may be employed.

A photo-curable composition of the present invention contains the bicarbazole compound (A) described in detail above and a photopolymerization initiator (B) as essential components. In the case where the photo-curable composition is cured in a radical polymerization system, another radical-polymerizable component (C) may be mixed in addition to the bicarbazole compound (A) and the photopolymerization initiator (B).

Examples of the other radical-polymerizable component (C) used in such a case include epoxy (meth)acrylates, fluorene skeleton-containing di(meth)acrylates, acrylate compounds having a polyoxyalkylene structure, other monofunctional (meth)acrylate monomers, and other polyfunctional (meth)acrylate monomers. In the present invention, as the radical-polymerizable component (C), the other monofunctional (meth)acrylate monomers and the other polyfunctional (meth)acrylate monomers are preferably used alone, or an epoxy (meth)acrylate, a fluorene skeleton-containing di(meth)acrylate, or an acrylate compound having a polyoxyalkylene structure is preferably used in combination with any of these monomers from the viewpoint of a reduction in the viscosity and realization of a high refractive index.

Specific examples of the epoxy (meth)acrylate include compounds obtained by allowing (meth)acrylic acid or an anhydride thereof to react with an epoxy resin. Specific examples of the epoxy resin that is allowed to react with (meth)acrylic acid or an anhydride thereof include diglycidyl ethers of a divalent phenol such as hydroquinone or catechol; diglycidyl ethers of a biphenol compound such as 3,3'-biphenyl diol or 4,4'-biphenyl diol; bisphenol epoxy resins such as a bisphenol A epoxy resin, a bisphenol B epoxy resin, a bisphenol F epoxy resin, or a bisphenol S epoxy resin; polyglycidyl ethers of a naphthol compound such as 1,4-naphthalene diol, 1,5-naphthalene diol, 1,6-naphthalene diol, 2,6-naphthalene diol, 2,7-naphthalene diol, binaphthol, or bis(2,7-dihydroxynaphthyl)methane; triglycidyl ethers of 4,4',4''-methylidynetrisphenol or the like; and novolac epoxy resins such as a phenol novolac epoxy resin and a cresol novolac epoxy resin.

Specific examples of the epoxy resin further include polyglycidyl ethers of a polyether-modified aromatic polyol, obtained by ring-opening polymerization of the biphenol compound, bisphenol A, bisphenol B, bisphenol F, bisphenol S, or a naphthol compound with a cyclic ether compound such as ethylene oxide, propylene oxide, tetrahydrofuran, ethyl glycidyl ether, propyl glycidyl ether, butyl glycidyl ether, phenyl glycidyl ether, or allyl glycidyl ether.

Specific examples of the epoxy resin further include polyglycidyl ethers of a lactone-modified aromatic polyol, obtained by polycondensation of the biphenol compound, bisphenol A, bisphenol B, bisphenol F, bisphenol S, or a naphthol compound with a lactone compound such as epsilon-caprolactone.

Among these, from the viewpoint that a cured product of an epoxy (meth)acrylate that is finally obtained has a high refractive index, epoxy resins having an aromatic ring skeleton in the molecular structure thereof are preferable. In particular, from the viewpoint of obtaining a cured coating film that has a higher refractive index and exhibits a high adhesive property to a plastic film substrate even under a high-temperature high-humidity condition, the bisphenol epoxy resins or the polyglycidyl ethers of a naphthol compound are more preferable, and the bisphenol epoxy resins are particularly preferable.

Among the bisphenol epoxy resins, epoxy resins having an epoxy equivalent in the range of 160 to 1,000 g/eq are preferable, and epoxy resins having an epoxy equivalent in the range of 165 to 600 g/eq are more preferable because a coating film having a higher refractive index and a higher hardness is obtained.

(Meth)acrylic acid or an anhydride thereof that is allowed to react with the epoxy resin is more preferably acrylic acid because, in particular, a photo-curable resin composition having good curability is obtained.

Next, a specific example of the fluorene skeleton-containing di(meth)acrylate is a compound represented by structural formula (7) below:

[Chem. 16]

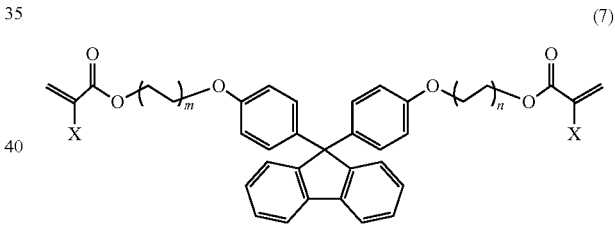

In structural formula (7), X is a hydrogen atom or a methyl group, and m and n are each independently an integer of 0 to 5.

The acrylate compounds having a polyoxyalkylene structure are compounds having polyoxyalkylene structure such as a polyethylene glycol chain or a polypropylene glycol in the molecular structures thereof. Examples thereof include diacrylates of polyethylene glycol having a number of ethylene oxide units of 4 to 15, monoacrylates of polyethylene glycol having a number of ethylene oxide units of 4 to 15, diacrylates of polypropylene glycol having a number of propylene oxide units of 4 to 15, monoacrylates of polypropylene glycol having a number of propylene oxide units of 4 to 15, ethylene oxide (EO)-modified glycerol triacrylates (the number of EO units: 3 to 10), propylene oxide (PO)-modified glycerol triacrylates (the number of PO units: 3 to 10), ethylene oxide-modified trimethylolpropane triacrylates (the number of EO units: 4 to 20), propylene oxide-modified trimethylolpropane triacrylates (the number of PO units: 4 to 20), diacrylate of an ethylene oxide adduct of bisphenol, the adduct having a number of ethylene oxide units of 4 to 15, and diacrylate of a propylene oxide adduct of bisphenol, the adduct having a number of propylene oxide units of 4 to 15.

Examples of the other monofunctional (meth)acrylate monomer include monofunctional (meth)acrylates such as n-butyl (meth)acrylate, isobutyl (meth)acrylate, tert-butyl (meth)acrylate, n-pentyl (meth)acrylate, n-hexyl (meth) acrylate, n-octyl (meth)acrylate, isooctyl (meth)acrylate, 2-ethylhexyl (meth)acrylate, benzyl (meth)acrylate, phenylbenzyl (meth)acrylate, phenoxyethyl (meth)acrylate, phenylthioethyl (meth)acrylate, o-phenylphenoxyethyl (meth) acrylate, naphthoxyethyl (meth)acrylate, naphthylthioethyl (meth)acrylate, phenoxydiethyleneglycol (meth)acrylate, glycidyl (meth)acrylate, morpholine (meth)acrylate, 2-hydroxyethyl (meth)acrylate, 2-hydroxypropyl (meth)acrylate, 4-hydroxybutyl (meth)acrylate, diethyleneglycol mono (meth)acrylate, triethyleneglycol mono(meth)acrylate, dipropyleneglycol mono(meth)acrylate, 2-methoxyethyl (meth)acrylate, methoxydiethyleneglycol (meth)acrylate, methoxytriethyleneglycol (meth)acrylate, methoxypolyethyleneglycol (meth)acrylate, 2-butoxyethyl (meth)acrylate, butoxytriethyleneglycol (meth)acrylate, 2-ethoxyethyl (meth)acrylate, 2-(2-ethoxyethoxy)ethyl (meth)acrylate, ethoxypolyethyleneglycol (meth)acrylate, 4-nonylphenoxyethylene glycol (meth)acrylate, tetrahydrofurfuryl (meth) acrylate, caprolactone-modified tetrahydrofurfuryl (meth) acrylate, cyclohexyl (meth)acrylate, isobornyl (meth) acrylate, 2-hydroxy-3-phenoxypropyl (meth)acrylate, cyclohexyl (meth)acrylate, cyclohexyl methyl (meth)acrylate, cyclohexyl ethyl (meth)acrylate, dicyclopentanyl (meth)acrylate, dicyclopentanyloxyethyl (meth)acrylate, dicyclopentenyl (meth)acrylate, dicyclopentenyloxyethyl (meth)acrylate, and phenylphenoxyethyl acrylate.

Examples of the other polyfunctional (meth)acrylate monomer include bifunctional (meth)acrylates such as ethylene glycol di(meth)acrylate, diethylene glycol di(meth) acrylate, triethylene glycol di(meth)acrylate, polyethylene glycol di(meth)acrylate, propylene glycol di(meth)acrylate, dipropylene glycol di(meth)acrylate, tripropylene glycol di(meth)acrylate, butylene glycol di(meth)acrylate, tetrabutylene glycol di(meth)acrylate, 1,4-butanediol di(meth)acrylate, 1,6-hexanediol di(meth)acrylate, 1,9-nonanediol di(meth)acrylate, neopentyl glycol di(meth)acrylate, di(meth)acrylate of an ethylene oxide adduct of bisphenol F, di(meth)acrylate of a propylene oxide adduct of bisphenol F, dicyclopentanyl di(meth)acrylate, glycerol di(meth)acrylate, neopentyl glycol hydroxypivalate di(meth)acrylate, caprolactone-modified neopentyl glycol hydroxypivalate di(meth) acrylate, tetrabromobisphenol A di(meth)acrylate, hydroxypivalaldehyde-modified trimethylolpropane di(meth)acrylate, and 1,4-cyclohexane dimethanol di(meth)acrylate; trifunctional (meth)acrylates such as trimethylolpropane tri(meth)acrylate, tri(meth)acrylate of an ethylene oxide adduct of trimethylolpropane, tri(meth)acrylate of a propylene oxide adduct of trimethylolpropane, pentaerythritol tri(meth)acrylate, glycerol tri(meth)acrylate, and tri (meth)acrylate of alkyl-modified dipentaerythritol; and tetrafunctional (meth)acrylates such as ditrimethylolpropane tetra(meth)acrylate, tetra(meth)acrylate of an ethylene oxide adduct of ditrimethylolpropane, and tetra(meth)acrylate of a propylene oxide adduct of ditrimethylolpropane.

In the case where an epoxy (meth)acrylate, a fluorene skeleton-containing di(meth)) acrylate, or an acrylate compound having a polyoxyalkylene structure is used, the mixing proportion thereof is preferably 10% to 70% by mass in polymerization components. In the case where the other monofunctional (meth)acrylate monomer or the other polyfunctional (meth)acrylate monomer is used, the mixing proportion thereof is preferably 10% to 70% by mass in polymerization components.

The photopolymerization initiator (B) used in the photocurable composition of the present invention may be a photo-radical polymerization initiator or a photo-cationic polymerization initiator. Examples of the photopolymerization initiator (B) include 1-hydroxycyclohexyl phenyl ketone, 2-hydroxy-2-methyl-1-phenylpropan-1-one, 1-[4-(2-hydroxyethoxy)phenyl]-2-hydroxy-2-methyl-1-propan-1-one, 2,2'-dimethoxy-1,2-diphenylethan-1-one, 2,4,6-trimethylbenzoyl diphenylphosphine oxide (TPO), bis(2,4,6-trimethylbenzoyl)phenylphosphine oxide, 2-methyl-1-[4-(methylthio)phenyl]-2-morpholino-1-propanone, 2-benzyl-2-dimethylamino-1-(4-morpholinophenyl)-butan-1-one, benzophenone, 4-methylbenzophenone, 4-phenylbenzophenone, 4-(4-methylphenylthio)benzophenone, thioxanthone, 2-isopropylthioxanthone, 4-isopropylthioxanthone, 2,4-dimethylthioxanthone, 2,4-diethylthioxanthone, 2,4-diisopropylthioxanthone, and 2,4-dichlorothioxanthone.

Among these photopolymerization initiators, 1-hydroxycyclohexyl phenyl ketone and 2,4,6-trimethylbenzoyl diphenylphosphine oxide are preferable from the viewpoint that the photopolymerization initiator is colorless and transparent and a plastic lens that is finally obtained has good transparency.

The mixing proportion of the photopolymerization initiator (B) described above is preferably in the range of 0.1 to 20 parts by weight, and more preferably in the range of 0.5 to 10 parts by weight relative to 100 parts by weight of the photo-curable composition.

The photo-curable composition of the present invention may contain, in addition to the components described above, a mold releasing agent, a defoaming agent, a leveling agent, a light stabilizer (such as an ultraviolet absorber or a hindered amine), an antioxidant, a polymerization inhibitor, an antistatic agent, a coloring agent (such as a dye or a pigment), an inorganic filler, an organic filler, and the like. The bicarbazole compound (A)-containing curable composition of the present invention contains the bicarbazole compound (A) having a high refractive index, and thus can be suitably used for a plastic lens, and furthermore, a plastic lens for an optical material.

A cured product of the photo-curable composition of the present invention has a refractive index of 1.600 or more, and preferably, 1.610 or more. When the refractive index is lower than 1.600, the refractive index is not sufficient for use in an optical material.

An example of a method for curing the photo-curable composition of the present invention is a method in which the composition is applied or molded onto a substrate according to the purpose and the use, and is then irradiated with light such as ultraviolet light or visible light. In the case where ultraviolet light is used, examples of a light source used in this method include mercury lamps such as an ultra-high-pressure mercury lamp, a high-pressure mercury lamp, and a low-pressure mercury lamp, a xenon lamp, a carbon arc, a metal halide lamp, and a high-output LED-UV lamp. In this case, the exposure of ultraviolet light is preferably in the range of 0.1 to 1,000 mJ/cm$^2$ from the viewpoint of good curability.

The photo-curable composition of the present invention described in detail above can be suitably used in plastic lenses such as a spectacle lens, a lens for a digital camera, a Fresnel lens, and a prism lens; and various optical materials such as an over-coating agent for optical use, a hard-coating agent, an antireflection film, an optical fiber, an optical waveguide, a hologram, a prism lens, an LED sealing material, and a coating material for a solar cell.

In particular, in view of the characteristics that the refractive index of the resulting cured product is high and the cured product has good heat resistance and good moisture resistance, the photo-curable composition of the present invention is preferably applied to a plastic lens, and in particular, among the above applications, a prism lens for a liquid crystal substrate.

Herein, the term "prism lens for a liquid crystal substrate" refers to a sheet-like lens including a sheet-like formed body and a plurality of fine prism-shaped portions provided on one surface of the sheet-like formed body. The sheet-like lens is usually arranged on a back surface (on the light source side) of a liquid crystal display element so that the prism surface faces the element side. A light guide sheet is further provided on the back surface. Alternatively, in the sheet-like lens, the prism lens may also function as the light guide sheet.

Regarding the shape of each of the prism portions of the prism lens, an angle (theta) of a prism apex angle is preferably in the range of 70 to 110 degrees from the viewpoint that a good light-condensing property is obtained and the brightness is improved. The angle (theta) of a prism apex angle is more preferably in the range of 75 to 100 degrees, and particularly preferably in the range of 80 to 95 degrees.

The pitch of the prism portions is preferably 100 micrometers or less and particularly preferably 70 micrometers or less from the viewpoint of preventing the generation of a moire pattern on a screen and further improving the definition of the screen. The height of the irregularities of the prism portions is determined by the angle (theta) of the prism apex angle and the pitch of the prism portions. The height is preferably 50 micrometers or less.

In order to produce the prism lens by using the composition of the present invention, for example, the following method may be employed. The composition is applied onto a mold such as a metal mold or resin mold on which a prism pattern is formed, and the surface of the composition is smoothed. Subsequently, a transparent substrate is overlapped thereon. The composition is irradiated with an active energy ray and cured, thus producing the prism lens.

When the transparent substrate has high transparency, the transparent substrate preferably has a thickness of 3 mm or less in consideration of the transmittance of active energy rays, handleability, etc. Examples of the material of the transparent substrate include synthetic resins such as acrylic resins, polycarbonate resins, polyester resins, polystyrene resins, fluororesins, polyimide resins, and mixtures of these polymers; and glass.

EXAMPLES

Embodiments of the present invention will now be described in more detail. However, the present invention is not limited thereto. The units are on a mass basis, unless otherwise stated.

[Measurement Conditions for Mass Spectrum]

Mass spectra were measured with "5937 MSD EI" manufactured by Agilent Technologies.

[Measurement Conditions for $^1$H-NMR]

Nuclear magnetic resonance (NMR) spectra were measured with "Avance 400" (400 MHz) manufactured by Bruker BioSpin K.K. Measurement condition: As a solvent, $d_6$-dimethyl sulfoxide (DMSO) was used.

Synthesis Example 1

Synthesis of 1,3'-bicarbazole

In a reaction vessel, 300 g (1.75 mol) of 1,2,3,4-tetrahydrocarbazole, 300 g of activated carbon, and 2,500 g of 1,2-dichlorobenzene were charged and allowed to react for 36 hours at a temperature of 140 to 170 degrees Celsius while air was bubbled (120 to 150 L/hr). The fact that 1,2,3,4-tetrahydrocarbazole charged as a material was completely consumed was confirmed by high-performance liquid chromatography (HPLC), and the reaction was terminated. The activated carbon was removed by filtration, and the reaction solution was concentrated. Thus, 360 g of a crude reaction product 1 containing 33.65% by mass of 1,3'-bicarbazole was obtained. The crude product was washed with ethanol at 70 degrees Celsius over a period of three hours. The resulting suspension was filtered and dried. Thus, 220 g of a crude reaction product 2 containing 42.61% by mass of 1,3'-bicarbazole was obtained (hereinafter, this product is abbreviated as "1,3'-bicarbazole composition 1").

Subsequently, 73 g of the crude reaction product 2 was purified by column chromatography, and the purified product was then washed with 100 mL of dichloromethane at room temperature for three hours. Thus, 8.7 g of 1,3'-bicarbazole having a purity of 90% by mass was obtained (where the remaining 10% by mass was constituted by carbazole). FIG. 1 shows a $^1$H-NMR chart of the prepared 1,3'-bicarbazole.

Example 1

Synthesis of 9,9'-diacryloyl-1,3'-bicarbazole

[Chem. 17]

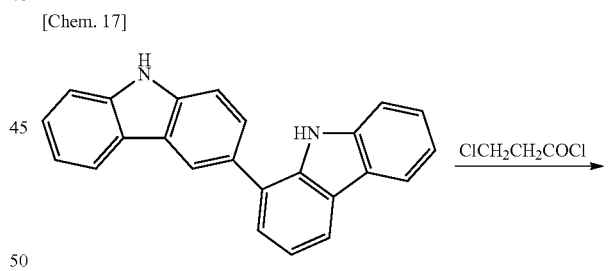

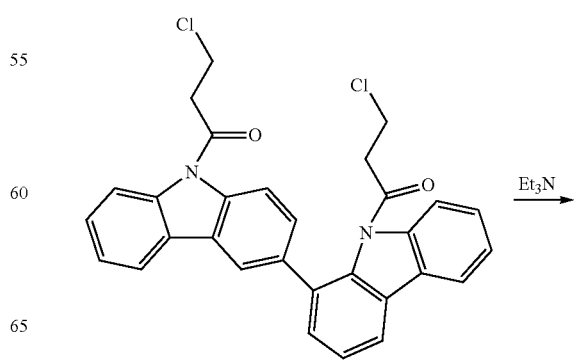

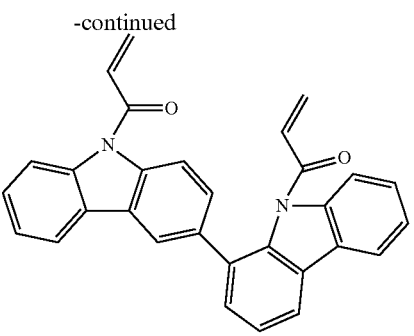

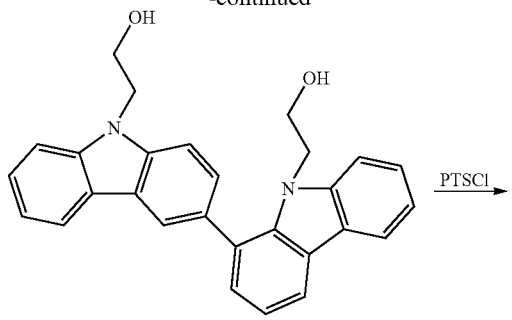

HEBIC

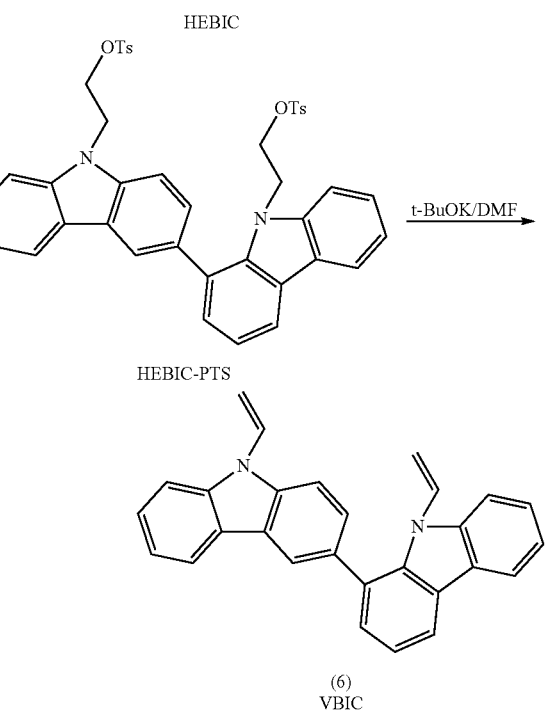

HEBIC-PTS (6)
VBIC

First, 5.0 g (15 mmol) of 1,3'-bicarbazole having a purity of 90% by mass and obtained in Synthesis Example 1 was suspended in 45.4 g (358 mmol) of 3-chloropropionyl chloride, and the resulting reaction mixture was allowed to react at 130 degrees Celsius for eight hours while hydrogen chloride gas generated was discharged with a nitrogen stream. The reaction mixture was cooled to room temperature, and 200 mL of toluene was added to the reaction mixture to dissolve the reaction product. The resulting solution was washed with water twice, a saturated sodium hydrogencarbonate solution once, and a saturated sodium chloride solution once in that order. The solution was then dried with anhydrous magnesium sulfate. The solvent was distilled off under reduced pressure, and the resulting product was then purified by silica gel column chromatography (n-heptane:ethyl acetate=9:1). Thus, 6.5 g of 9,9'-bis(3-chloropropionyl)-1,3'-bicarbazole was obtained in the form of a white crystal.

Figure 2:
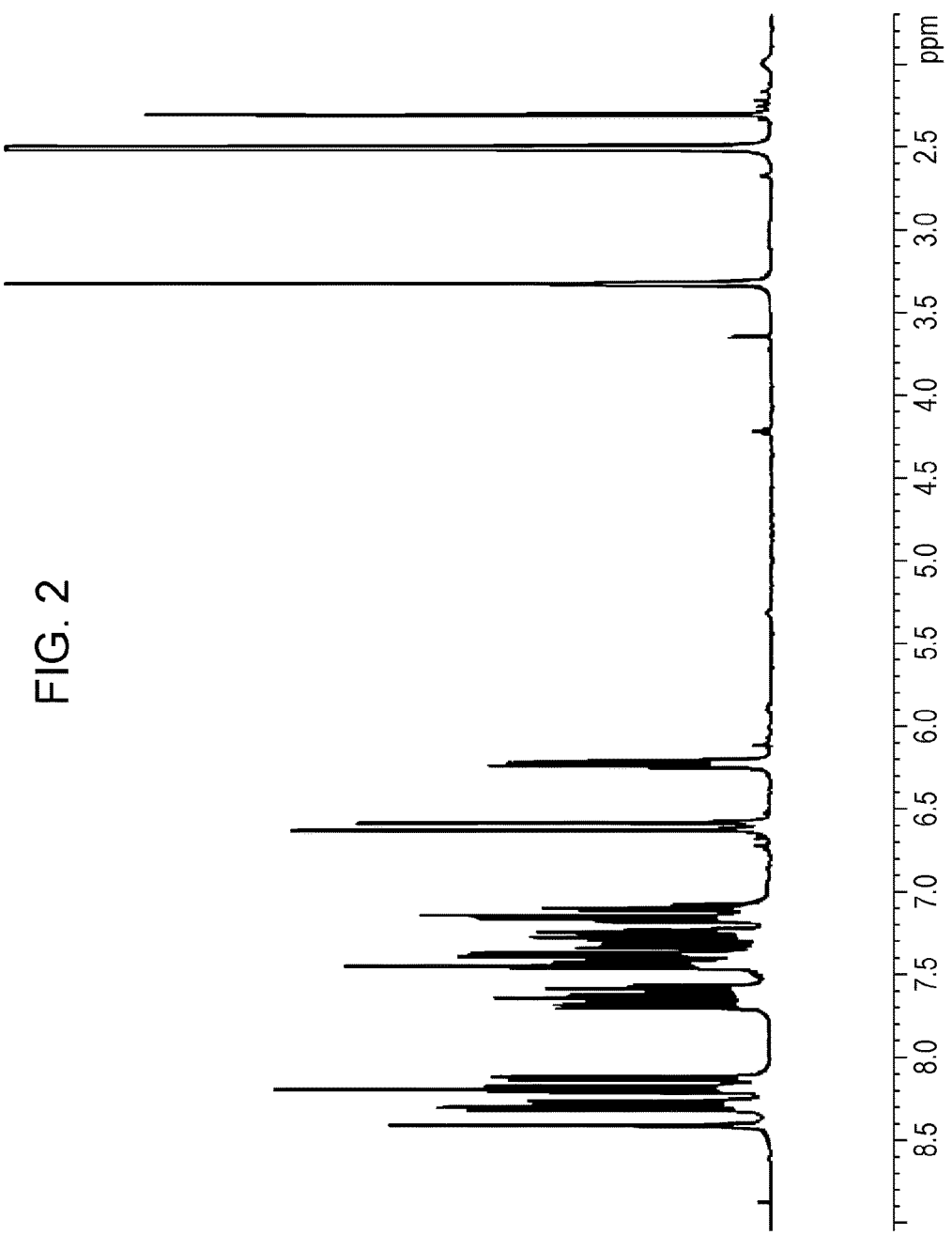
FIG. 2 is a $^1$H-NMR chart of 9,9'-diacryloyl-1,3'-bicarbazole prepared in Example 1.

Subsequently, in a 300-mL three-necked flask, 6.0 g of 9,9'-bis(3-chloropropionyl)-1,3'-bicarbazole and 0.2 g of 4-methoxyphenol were dissolved in 60 mL of toluene. Next, 2.37 g (23.4 mmol) of triethylamine was added to this solution while stirring, and the reaction solution was allowed to react at 60 degrees Celsius for four hours. The reaction solution was cooled to room temperature, and 200 mL of toluene was added thereto. The solution was washed with a saturated sodium chloride solution once, 2% hydrochloric acid once, a saturated sodium hydrogencarbonate solution once, and a saturated sodium chloride solution once in that order. The solution was dried with anhydrous magnesium sulfate. The solvent was then distilled off under reduced pressure, and the resulting crude product was purified by silica gel column chromatography (n-heptane:ethyl acetate=9:1). Thus, 5.1 g of 9,9'-diacryloyl-1,3'-bicarbazole was obtained in the form of a white crystal. A mass spectrum of the 9,9'-diacryloyl-1,3'-bicarbazole was measured. According to the result, peaks at m/z of 440, 386, and 332 were observed. FIG. 2 shows a $^1$H-NMR chart of the 9,9'-diacryloyl-1,3'-bicarbazole.

Example 2

Synthesis of 9,9'-divinyl-1,3'-bicarbazole

[Chem. 18]

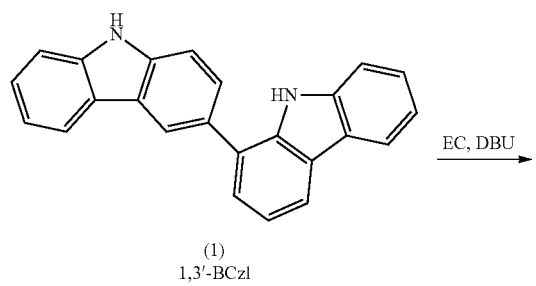

(1)
1,3'-BCzl

Synthesis of 9,9'-bis(hydroxyethyl)-1,3'-bicarbazole

In a flask equipped with a thermometer, a condenser tube, and a stirrer, 3.5 g (10.5 mmol, purity: 90% by mass) of 1,3'-bicarbazole prepared in Synthesis Example 1, 3.8 g (25.3 mmol) of 1,8-diazabicyclo[5.4.0]-7-undecene (DBU), and 5.1 g (58 mmol) of ethylene carbonate were dissolved in 10 mL of dimethylformamide (DMF). The reaction mixture was allowed to react in a nitrogen atmosphere while heating at 110 degrees Celsius for six hours. The reaction mixture was cooled to room temperature, and then diluted with 50 mL of ethanol. Furthermore, this diluted solution was poured into 300 mL of distilled water, and the resulting dispersion liquid was stirred for 30 minutes without further treatment. The resulting solid obtained after filtration was dried. Thus, 5.0 g of 9,9'-bis(hydroxyethyl)-1,3'-bicarbazole (HEBIC) having a purity of 87% was obtained.

Subsequently, in a flask equipped with a thermometer, a condenser tube, and a stirrer, 5.0 g of HEBIC prepared above, 10 g (94.3 mmol) of anhydrous potassium carbonate, and 9.12 g (48 mmol) of para-toluenesulfonyl chloride were dissolved in 50 mL of methylene chloride, and 4.8 g of triethylamine was added dropwise to the solution over a period of 10 minutes. The reaction mixture was stirred at room temperature for one night to complete the reaction. A salt produced as a by-product was separated by filtration. Next, 100 mL of ethyl acetate was added to the resulting filtrate. The filtrate was washed with a 2% hydrochloric acid solution and then neutralized with a saturated aqueous solution of sodium hydrogencarbonate until the pH of the filtrate became 7. The filtrate was dehydrated with anhydrous magnesium sulfate, and then concentrated under reduced pressure. Thus, 8.5 g of 9,9'-bis(tosyloxyethyl)-1,3'-bicarbazole (HEBIC-PTS) having a purity of 85% was obtained. The resulting crude product was purified by silica gel column chromatography (n-heptane:ethyl acetate=3:1). Thus, 5.4 g of HEBIC-PTS was obtained.

Figure 3:
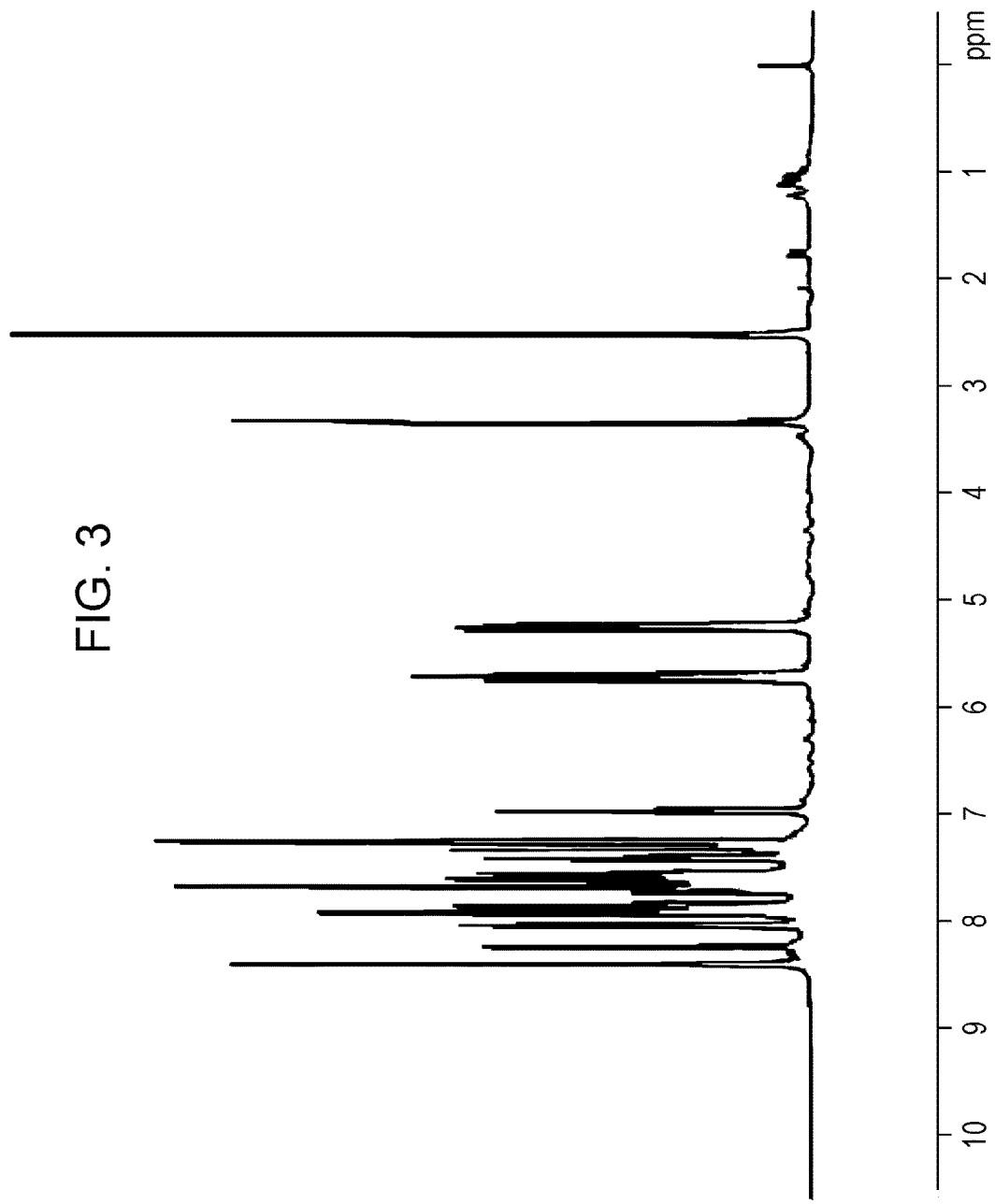
FIG. 3 is a $^1$H-NMR chart of 9,9'-divinyl-1,3'-bicarbazole prepared in Example 2.

Subsequently, in a flask equipped with a thermometer, a dropping funnel, and a stirrer, 1.5 g (13.4 mmol) of potassium-tert-butoxide was dissolved in 20 mL of DMF. To this solution, a solution prepared by dissolving 2.8 g of HEBIC-PTS in 10 mL of DMF was added dropwise over a period of 10 minutes, and the resulting mixture was stirred at room temperature for two hours. Next, 100 mL of a 2% aqueous hydrochloric acid solution was added to the mixture to terminate the reaction, and the mixture was further stirred for one hour. A produced pale yellow crystal was collected by filtration and dissolved in 20 mL of methylene chloride. Subsequently, 50 mL of ethanol was added to this solution, and methylene chloride was distilled off under vacuum to precipitate a crystal of 9,9'-divinyl-1,3'-bicarbazole (VBIC). The crystal was filtered and dried. Thus, 0.6 g of 9,9'-divinyl-1,3'-bicarbazole was obtained in the form of a pale yellow crystal. A mass spectrum of the 9,9'-divinyl-1,3'-bicarbazole was measured. According to the result, a peak at m/z of 384 was observed. FIG. 3 shows a $^1$H-NMR chart of the 9,9'-divinyl-1,3'-bicarbazole.

Example 3

Synthesis of 9,9'-bis(acryloyloxyethyl)-1,3'-bicarbazole

[Chem. 19]

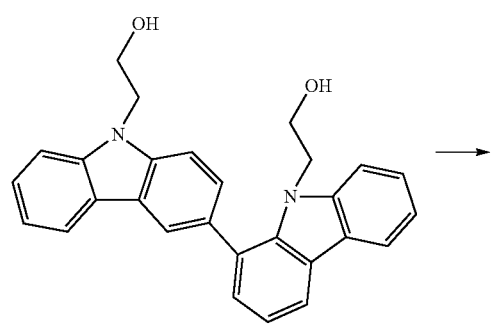

→

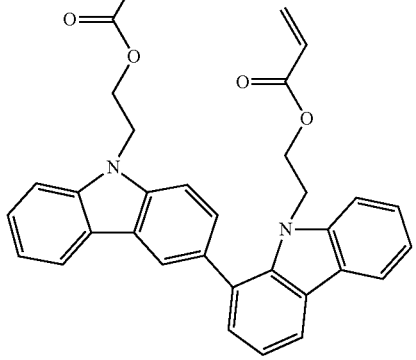

Figure 4:
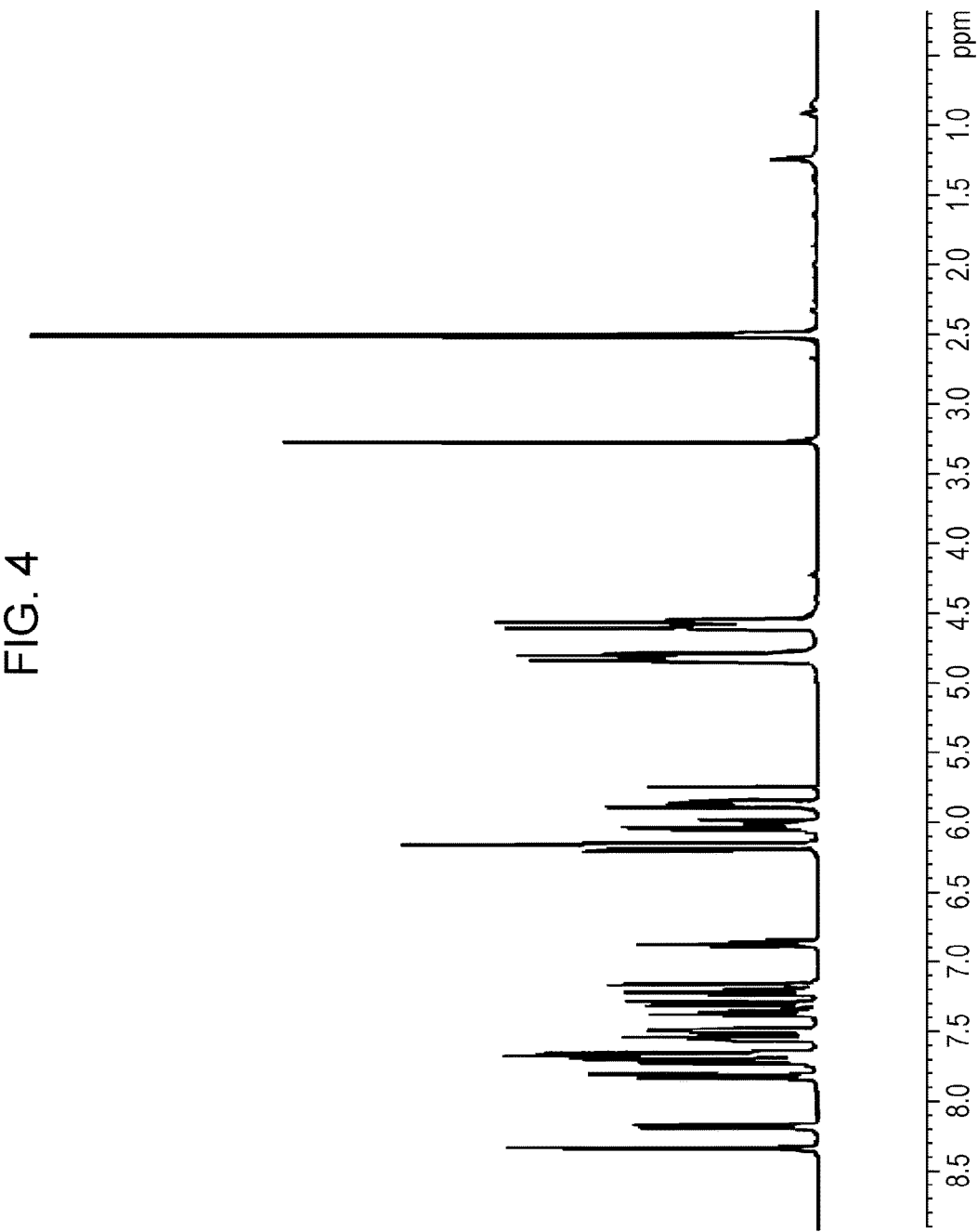
FIG. 4 is a $^1$H-NMR chart of 9,9'-bis(acryloyloxyethyl)-1,3'-bicarbazole prepared in Example 3.

In a flask equipped with a thermometer, a condenser tube, and a stirrer, 4.3 g of 9,9'-bis(hydroxyethyl)-1,3'-bicarbazole obtained as an intermediate product of Example 2, 4.5 g (63 mmol) of acrylic acid, and 0.2 g (1.6 mmol) of 4-dimethylaminopyridine were dissolved in 50 mL of methylene chloride. The solution was cooled to 5 degrees Celsius, and 7.9 g (63 mmol) of N,N'-diisopropylcarbodiimide was added dropwise to the solution over a period of 20 minutes. After the dropwise addition, the reaction temperature was increased to room temperature, and the reaction mixture was stirred at room temperature for one night to complete the reaction. A solid in the resulting reaction mixture was removed by filtration, and the resulting filtrate was concentrated under reduced pressure. The resulting crude product was then purified by silica gel column chromatography (n-heptane:ethyl acetate=5:1). Thus, 3.0 g of 9,9'-bis(acryloyloxyethyl)-1,3'-bicarbazole was obtained. A mass spectrum of the 9,9'-bis(acryloyloxyethyl)-1,3'-bicarbazole was measured. According to the result, a peak at m/z of 528 was observed. FIG. 4 shows a $^1$H-NMR chart of the 9,9'-bis(acryloyloxyethyl)-1,3'-bicarbazole.

Comparative Example 1

Synthesis of 9-vinylcarbazole

First, 100.3 g (0.6 mol) of carbazole and 264.2 g (3.0 mol) of ethylene carbonate were suspended in 120 mL of N,N-dimethylformamide, and the resulting mixture was stirred. Next, 109.6 g (0.72 mol) of 1,8-diazabicyclo[5.4.0]-7-undecene was added to the mixture. Stirring was conducted for two hours while the internal temperature of the resulting solution was maintained at 100 degrees Celsius. The solution was then cooled. Ethyl acetate and water were added to the solution, and a reaction product was extracted into an organic layer. After a liquid separation operation, ethyl acetate in the organic layer was concentrated. Subsequently, 750 mL of acetonitrile was added thereto and the resulting solution was stirred. Next, 94.9 g (1.2 mol) of pyridine was added to the solution, and 116.8 g (1.02 mol) of methanesulfonyl chloride was added dropwise thereto over a period of 20 minutes while the internal temperature of the solution was maintained at 20 to 25 degrees Celsius. Subsequently, stirring was conducted in this temperature range for two hours. After the reaction, 750 mL of water was added to the solution, and a produced precipitate was filtered with suction. Thus, 151.1 g of 2-(9-carbazolyl)ethylmethane sulfonate was obtained. Next, 92.6 g (0.32 mol) of 2-(9- carbazolyl)ethylmethane sulfonate and 0.64 g of hydroquinone were suspended in 320 mL of N,N-dimethylformamide, and the resulting suspension was stirred. Next, 26.1 g (0.384 mol) of sodium ethoxide was added thereto, and stirring was conducted for 30 minutes while the internal temperature of the resulting solution was maintained at 10 degrees Celsius. Subsequently, 320 mL of water was added thereto, and a produced precipitate was filtered with suction. Thus, 58.7 g of a target product, i.e., 9-vinylcarbazole was obtained.

Comparative Example 2

Synthesis of 3,3'-bicarbazole

[Chem. 20]

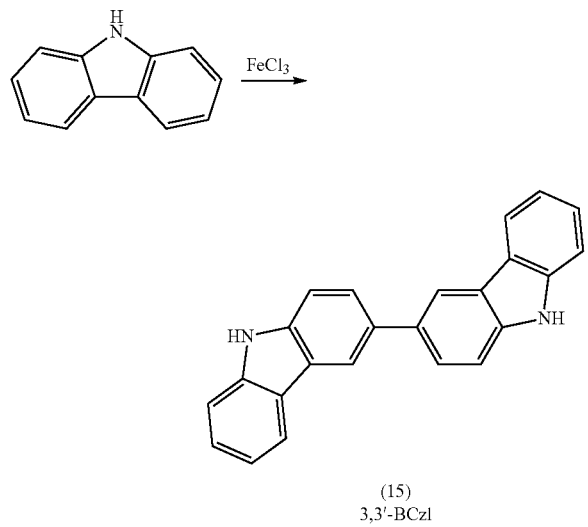

(15)
3,3'-BCzl 3,3'-Bicarbazole was synthesized by the method described in a known document "Molecular Crystals and Liquid Crystals 2008, vol. 492, pp. 241-253".

[Refractive Index]

Table 1 shows refractive indices of the compounds obtained in Examples 1 to 3, Synthesis Example 1, and Comparative Examples 1 and 2. The refractive index of each of the compounds was determined as follows. A compound was diluted with N-methylpyrrolidone (NMP) to prepare three samples having different concentrations. Liquid refractive indices of the respective solutions were measured, and the measured data was extrapolated to calculate the refractive index.

TABLE 1

| Compound | | Liquid refractive index |
|---|---|---|
| Example 1 | 9,9'-Diacryloyl-1,3'-bicarbazole | 1.723 |
| Example 2 | 9,9'-Divinyl-1,3'-bicarbazole | 1.735 |
| Example 3 | 9,9'-Bis(acryloyloxyethyl)-1,3'-bicarbazole | 1.664 |
| Synthesis Example 1 | 1,3'-Bicarbazole | 1.76 |

TABLE 1-continued

| Compound | | Liquid refractive index |
|---|---|---|
| Comparative Example 1 | 9-Vinylcarbazole | 1.674 |
| Comparative Example 2 | 3,3'-Bicarbazole | 1.765 |

Measuring device: Abbe refractometer NRA-2T, manufactured by Atago Co., Ltd.
Measurement wavelength: 589 nm (D line)
[Solubility]
Table 2 shows evaluation results of solubility of each of the compounds obtained in Examples 1 to 3, Synthesis Example 1, and Comparative Examples 1 and 2. The solubility was evaluated on the basis of whether a compound was soluble or insoluble in o-phenylphenoxyethyl acrylate. The evaluation was performed at two levels at which the compound concentration was 10% by mass and 50% by mass.
(Evaluation Criteria)
A: Soluble
B: Insoluble

TABLE 2

| | Compound | 10 mass % | 50 mass % |
|---|---|---|---|
| Example 1 | 9,9'-Diacryloyl-1,3'-bicarbazole | A | B |
| Example 2 | 9,9'-Divinyl-1,3'-bicarbazole | A | A |
| Example 3 | 9,9'-Bis(acryloyloxyethyl)-1,3'-bicarbazole | A | A |
| Synthesis Example 1 | 1,3'-Bicarbazole | A | B |
| Comparative Example 1 | 9-Vinylcarbazole | A | B |
| Comparative Example 2 | 3,3'-Bicarbazole | B | B |

As shown in Tables 1 and 2, 1,3'-bicarbazole derivatives have significantly high refractive indices, and further have good solubility necessary for curable compositions.

Examples 4 to 7 and Comparative Examples 3 and 4

Active energy ray curable resin compositions were prepared in accordance with the compositions shown in Table 3 below, and liquid refractive indices were measured by the method described above.
[Method for Preparing Cured Product Sheet]
An ultraviolet curable resin composition was applied onto a polyester film which had been subjected to an adhesion improving treatment (A-4300, manufactured by Toyobo Co., Ltd, film thickness: 188 micrometers) using an applicator. The resulting film was irradiated with ultraviolet light of 1,000 mJ/cm$^2$ in a nitrogen atmosphere by using a conveyor-type ultraviolet irradiation device including a high-pressure mercury lamp. Thus, a film including a cured film (10 to 15 micrometers) was prepared.
[Curability]
When the cured film prepared by the above method for preparing a cured product sheet did not have tackiness, the cured film was evaluated as "A". When the cured film had tackiness, the cured film was evaluated as "B".
[Transparency]
A light transmittance of the cured film prepared by the above method for preparing a cured product sheet was measured in the wavelength range of 400 to 800 nm. When the transmittance was 85% or more in the whole range, the cured film was evaluated as "A". When the transmittance was lower than 85%, the cured film was evaluated as "B".

TABLE 3

|  |  | Example 4 | Example 5 | Example 6 | Example 7 | Comparative Example 3 | Comparative Example 4 |
|---|---|---|---|---|---|---|---|
| Polymerization component | 9,9'-Diacryloyl-1,3'-bicarbazole | 20 | | | | | |
|  | 9,9'-Divinyl-1,3'-bicarbazole | | 20 | | 20 | | |
|  | 9,9'-Bis(acryloyloxyethyl)-1,3'-bicarbazole | | | 40 | | | |
|  | FDA | | | | 20 | 20 | |
|  | OPPEA | 80 | 80 | 60 | 60 | 80 | 80 |
|  | 9-Vinylcarbazole | | | | | | 20 |
| Polymerization initiator | Lucirin TPO | 2 | 2 | 2 | 3 | 2 | 2 |
|  | Irg 184 | 5 | 5 | 5 | 5 | 5 | 5 |
| Evaluation | Liquid refractive index | 1.603 | 1.615 | 1.621 | 1.626 | 1.584 | 1.595 |
|  | Curability | A | A | A | A | A | A |
|  | Transparency | A | A | A | A | A | A |

Footnotes of Table 3
FDA: bisphenoxyethanolfluorene diacrylate
OPPEA: o-phenylphenoxyethyl acrylate
Lucirin TPO: 2,4,6-trimethylbenzoyl diphenylphosphine oxide
Irg 184: 1-hydroxycyclohexyl phenyl ketone

The invention claimed is:

1. A bicarbazole compound represented by structural formula (1):

[Chem. 1]

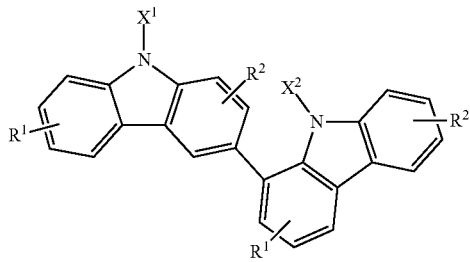

(wherein $X^1$ and $X^2$ are each independently a photopolymerizable functional group, a structural site having a photopolymerizable functional group, or a hydrogen atom, at least one of $X^1$ and $X^2$ is a photopolymerizable functional group or a structural site having a photopolymerizable functional group, $R^1$ and $R^2$ are each independently a hydrogen atom, an alkyl group having 1 to 4 carbon atoms, an alkoxy group having 1 to 4 carbon atoms, a bromine atom, or a chlorine atom, and at least one of $R^1$ and $R^2$ is a hydrogen atom).

2. The bicarbazole compound according to claim 1, wherein the photopolymerizable functional group in structural formula (1) is a vinyl group, a glycidyl group, a 2-methylglycidyl group, 3-methyloxetanyl-methyl group, 3-ethyloxetanyl-methyl group, or a (meth)acryloyl group-containing structural site represented by structural formula (2):

[Chem. 2]

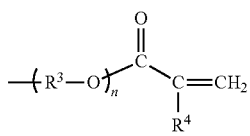

(wherein $R^3$ represents a linear or branched alkylene group having 2 to 6 carbon atoms, $R^4$ represents hydrogen atom or a methyl group, and n represents an integer of 0 to 10).

3. A method for producing a 1,3'-bicarbazole compound, wherein a 1,2,3,4-tetrahydrocarbazole represented by structural formula (4):

[Chem. 3]

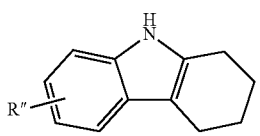

(wherein R" represents a hydrogen atom, an alkyl group having 1 to 4 hydrogen atoms, an alkoxy group having 1 to 4 hydrogen atoms, a bromine atom, or a chlorine atom.)
is subjected to an oxidation reaction in the presence of activated carbon.

4. A method for producing the bicarbazole compound according to claim 1, the method comprising: Step 1 in which a 1,2,3,4-tetrahydrocarbazole represented by structural formula (4):

[Chem. 4]

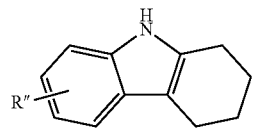

(wherein R" represents a hydrogen atom, an alkyl group having 1 to 4 hydrogen atoms, an alkoxy group having 1 to 4 hydrogen atoms, a bromine atom, or a chlorine atom.)
is subjected to an oxidation reaction in the presence of activated carbon; and
Step 2 in which various photopolymerizable functional groups are introduced into a reaction product obtained in Step 1.

5. The 1,3'-bicarbazole compound produced by the method according to claim 3.

6. A photo-curable composition comprising, as essential components, the bicarbazole compound (A) according to claim 1, and a photopolymerization initiator (B).

7. A cured product obtained by curing the photo-curable composition according to claim 6.

8. A plastic lens obtained by curing the curable composition according to claim 6.

9. The bicarbazole compound produced by the method according to claim 4.

10. A photo-curable composition comprising, as essential components, the bicarbazole compound (A) according to claim 2, and a photopolymerization initiator (B).

11. A photo-curable composition comprising, as essential components, the bicarbazole compound (A) according to claim 5, and a photopolymerization initiator (B).

12. A photo-curable composition comprising, as essential components, the bicarbazole compound (A) according to claim 9, and a photopolymerization initiator (B).

13. A cured product obtained by curing the photo-curable composition according to claim 10.

14. A cured product obtained by curing the photo-curable composition according to claim 11.

15. A cured product obtained by curing the photo-curable composition according to claim 12.

16. A plastic lens obtained by curing the curable composition according to claim 10.

17. A plastic lens obtained by curing the curable composition according to claim 11.

18. A plastic lens obtained by curing the curable composition according to claim 12.

* * * * *